United States Patent [19]

Berdahl

[11] Patent Number: 4,780,544
[45] Date of Patent: Oct. 25, 1988

[54] METHOD FOR MAKING OXYBISPHTHALIMIDES

[75] Inventor: Donald R. Berdahl, Scotia, N.Y.

[73] Assignee: General Electric Company, Schenectady, N.Y.

[21] Appl. No.: 881,415

[22] Filed: Jul. 2, 1986

[51] Int. Cl.[4] .......................................... C07D 209/48
[52] U.S. Cl. .................... 548/461; 548/476; 548/480; 548/481
[58] Field of Search ........................................ 548/461

[56] References Cited

U.S. PATENT DOCUMENTS 3,992,406  11/1976  Markezich ........................... 548/461
4,054,577  10/1977  Relles et al. ........................ 548/461
4,558,164  12/1985  Jones et al. ........................ 568/585

FOREIGN PATENT DOCUMENTS 0107542   2/1984  European Pat. Off. ............ 534/461
55-122738  9/1980  Japan .
55-136246 10/1980  Japan .

OTHER PUBLICATIONS

G. S. Kolesnikov, O. Ya. Fedotova, E. I. Hofbauer and V. G. Shelgayeva, "Synthesis and Study of Polyamido Acids Based on Diphenyloxide 3,4,3',4'-Tetracarboxylic Dianhydride and Certain Aromatic Diamines", Mendeleyev Institute of Chemical Technology, Moscow, Russia.

R. L. Markezich and O. S. Zemek, II, "Reactions of Fluoride and Nitrite Ions with 4-Nitrophthalimides", J. Org. Chem., vol. 42, No. 21 (1977), pp. 3431-3434.

Primary Examiner—Floyd D. Higel
Attorney, Agent, or Firm—William A. Teoli; James C. Davis, Jr.; James Magee, Jr.

[57] ABSTRACT

A method is provided for making oxybisphthalimides by heating an N-organonitrophthalimide in the presence of an aprotic organic solvent in an alkali metal carboxylate.

6 Claims, No Drawings

METHOD FOR MAKING OXYBISPHTHALIMIDES

BACKGROUND OF THE INVENTION

Prior to the present invention, a method for making bisimides was shown by Markezich et al, "Reactions of Fluoride and Nitrite Ions with 4-Nitrophthalimides", Journal of Organic Chemistry, 42, 3431 (1977), involving reactions of 4-nitro-N-methylphthalimide with either fluoride or nitrite salts in a dipolar aprotic solvent, affording up to a 78% yield of the corresponding diarylether, 4,4'-oxybis(N-methylphthalimide). Although high yields of diarylether can be obtained utilizing certain alkali nitrite salts or alkali fluoride salts, reaction times of 18–20 hours are often required.

In Jones et al, U.S. Pat. No. 4,558,164, a method for making symmetrical dinitrodiphenyl ethers is shown using halonitrobenzenes and a mixture of potassium acetate and potassium carbonate. However, side reactions have been found to occur in the Jones et al method rendering this procedure unsuitable for ether bisimide formation.

The present invention is based on my discovery that nitrophthalimides of the formula,

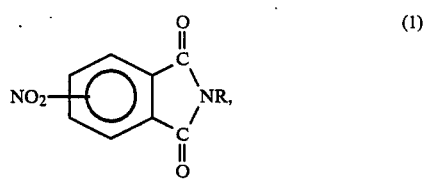

(1)

where R is a $C_{(1-14)}$ monovalent organic radical, can be converted to the corresponding bisimide of the formula

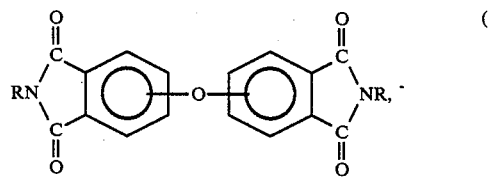

(2)

with yields as high as 80% and reaction time as little as 7.5 hours, by heating the nitrophthalimide in the presence of a dipolar aprotic solvent and an effective amount of alkali metal carboxylate.

STATEMENT OF THE INVENTION

There is provided by the present invention, a method for making bisimide which comprises (1) heating nitrophthalimide of Formula 1 to a temperature in the range of from about 100° C. to 400° C. in the presence of dipolar aprotic solvent and an effective amount of alkali metal carboxylate, and (2) recovering bisimide of Formula 2 from the resulting mixture of (1).

Radicals which can be included by R of formula 1, are, for example, monovalent $C_{(1-14)}$ alkyl radicals and monovalent $C_{(6-14)}$ aromatic hydrocarbon radicals or $C_{(6-14)}$ aromatic hydrocarbon radicals substituted with monovalent radicals such as halo, nitro, alkyl which are neutral during reaction.

There are included among the nitrophthalimide of Formula 1, compounds such as 4-nitro-N-methylphthalimide, 3-nitro-N-methylphthalimide and 4-nitro-N-phenylphthalimide.

There are included by the bisimide of Formula 2 compounds such as 4,4'-oxybis-N-methylphthalimide, 3,3'-oxybis-N-methylphthalimide and 4,4'-oxybis-N-phenylphthalimide.

Alkali metal carboxylate salts which can be utilized in the practice of the invention are, for example, potassium acetate, potassium benzoate, potassium propionate, sodium acetate, sodium benzoate, cesium acetate and cesium benzoate.

Preferably, there is utilized potassium alkyl carboxylate salts and cesium alkyl carboxylate salts.

Dipolar aprotic solvents which can be employed in the practice of the invention are, for example, N,N-dimethylformamide, dimethylsulfoxide, 1-methyl-2-pyrrolidinone, 1-cyclohexyl-2-pyrrolidinone, N,N-dimethylacetamide, tetramethylurea, and sulfolane.

In the practice of the present invention, the nitrophthalimide is heated in the presence of the dipolar aprotic solvent and an effective amount of the alkali metal carboxylate. An effective amount of the alkali metal carboxylate is 0.25 to 1.0 mole of alkali metal carboxylate, per mole of nitrophthalimide. The reaction is preferably conducted under substantially anhydrous conditions with agitation utilizing mixtures of from 3% solids to 50% solids based on the weight of total reaction mixture.

It is preferred to conduct the reaction under a nitrogen atmosphere. Reaction times of from 7 hours to 30 hours can be employed.

In order that those skilled in the art will be better able to practice the invention, the following examples are given by way of illustration and not by way of limitation. All parts are by weight.

EXAMPLE 1

A mixture of 2.64 g (12.8 mmol) of 4-nitro-N-methylphthalimide, 0.63 g, (6.4 mmol) of anhydrous potassium acetate and 14.4 mL of dimethylformamide which had been dried over 4 $A^O$ molecular sieves was flushed with nitrogen and heated to reflux until HPLC analysis showed the complete disappearance of starting material (7.5 hours). The mixture was cooled to room temperature and was poured into 0.2N HCl (80 mL), stirred for several minutes, filtered and dried. There was obtained 1.75 g or an 81% yield of 4,4'-oxybis-N-methylphthalimide as a tan solid. Recrystallization from glacial acetic acid resulted in a pale yellow solid melting point 266°–268.5° C.

EXAMPLE 2

The procedure of Example 1 was repeated except that various alkali metal carboxylate salts were employed to determine their effectiveness in converting the nitrophthalimide to the corresponding bisimide with respect to yield and reaction time. The following results were obtained where "BI" is bisimide:

TABLE I

| Carboxylate | Conditions | Yield BI (%, Isolated) |
|---|---|---|
| Sodium Acetate | DMF, 20 h[a,b] | 63[a], 66[b] |
| Sodium Propionate | DMF, 23 h[b] | 70 |
| Sodium Stearate | DMF, 22 h[b] | —[c] |
| Sodium Benzoate | DMF, 28 h[a] | 79 |
| Sodium Formate | DMF, 17 h[a] | 16 |
| Sodium 4-Hydroxybutyrate | DMF, 15 h[a] | 77 |
| Sodium Oxalate | DMF, 21 h[a] | 0 |

TABLE I-continued

| Carboxylate | Conditions | Yield BI (%, Isolated) |
| --- | --- | --- |
| Sodium Trifluoroacetate | DMF, 21 h[a] | 0 |
| Sodium 4-Aminobutyrate | DMF, 12.5 h[a] | 41 |
| Potassium Acetate | DMF, 7.5 h[b] | 80 |
| Potassium Propionate.H$_2$O | DMF, 7.25 h[b] | 65 |
| Potassium Benzoate.3H$_2$O | DMF, 30 h[b] | 75 |
| Potassium Carbonate | DMF, 17 h[a] | 16[d] |
| Lithium Benzoate | DMF, 57 h[b] | 71 |
| Cesium Acetate | DMF, 7.5 h[b] | 62 |
| Cesium Propionate | DMF, 7.5 h[b] | 63 |
| Potassium Nitrite | DMF, 17 h[b] | 81 |

[a]Reactions done on 3% solids.
[b]Reactions done on 20% solids.
[c]Soapy reaction mixture unable to be filtered successfully.
[d]HPLC yield.

The above results show that the alkylcarboxylate salts of potassium and cesium are the most effective catalysts. In addition, a comparison was made with potassium nitrite to show the effectiveness of the prior art catalyst.

Although the above examples are directed to only a few of the very many variables which can be used in the practice of the method of the present invention, it should be understood that the method of the present invention is directed to a much broader variety of alkali metal carboxylates, aprotic solvents and nitrophthalimides as shown in the description preceding these examples.

I claim:

1. A method for making oxybisphthalimide which comprises (1) heating nitrophthalimide of the formula

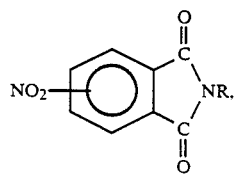

to a temperature in the range of from 100° C. to 400° C. in the presence of dipolar aprotic solvent and an effective amount of an alkali metal carboxylate selected from the class consisting of potassium alkylcarboxylates and cesium alkylcarboxylates, and (2) recovering oxybisphthalimide, from the resulting mixture of (1), where R is C$_{(1-14)}$ monovalent organic radical selected from the class consisting of alkyl radicals, aromatic hydrocarbon radicals, and aromatic hydrocarbon radicals substituted with a member selected from the class consisting of halo, nitro, and alkyl radicals.

2. A method in accordance with claim 1, where the alkali metal carboxylate is potassium acetate.

3. A method in accordance with claim 1, where the alkali metal carboxylate is cesium acetate.

4. A method in accordance with claim 1, where the alkali metal carboxylate is potassium propionate.

5. A method in accordance with claim 1, where the alkali metal carboxylate is cesium propionate.

6. A method in accordance with claim 1, where the aprotic solvent is dimethylformamide.

* * * * *